(12) United States Patent
Mangan et al.

(10) Patent No.: US 8,213,024 B2
(45) Date of Patent: Jul. 3, 2012

(54) METHOD AND SYSTEM FOR AERIAL IMAGING OF A RETICLE

(75) Inventors: Shmuel Mangan, Rehovot (IL); Boris Goldberg, Ashdod (IL); Ishai Schwarzband, Or-Yehuda (IL); On Haran, Kfar-Saba (IL); Michael Ben-Yishay, Natanya (IL); Amir Sagiv, Beit-Zayit (IL); Chaim Braude, Rehovot (IL)

(73) Assignee: Applied Materials Israel, Ltd., Rehovot (IL)

( * ) Notice: Subject to any disclaimer, the term of this patent is extended or adjusted under 35 U.S.C. 154(b) by 291 days.

(21) Appl. No.: 11/831,100

(22) Filed: Jul. 31, 2007

(65) Prior Publication Data
US 2008/0074659 A1 Mar. 27, 2008

Related U.S. Application Data

(60) Provisional application No. 60/821,056, filed on Aug. 1, 2006.

(51) Int. Cl.
*G01B 11/14* (2006.01)
*G01N 21/21* (2006.01)

(52) U.S. Cl. .................. 356/625; 356/237.1
(58) Field of Classification Search .... 356/237.2–237.6, 356/364–370
See application file for complete search history.

(56) References Cited

U.S. PATENT DOCUMENTS

| | | | | |
|---|---|---|---|---|
| 4,614,427 A * | 9/1986 | Koizumi et al. | ........... | 356/237.1 |
| 5,585,916 A * | 12/1996 | Miura et al. | ............... | 356/237.4 |
| 6,657,736 B1 * | 12/2003 | Finarov et al. | ............... | 356/625 |
| 6,665,065 B1 * | 12/2003 | Phan et al. | ............... | 356/237.1 |
| 6,995,847 B2 * | 2/2006 | Fashant et al. | ............... | 356/445 |
| 7,301,649 B2 * | 11/2007 | Fabrikant et al. | ............. | 356/625 |
| 7,418,124 B2 * | 8/2008 | Peterson et al. | ............... | 382/144 |
| 2001/0055416 A1 * | 12/2001 | Yamashita | ............... | 382/149 |
| 2004/0140418 A1 | 7/2004 | Ye et al. | | |
| 2005/0280806 A1 * | 12/2005 | Oomori et al. | ............. | 356/237.2 |
| 2006/0066843 A1 * | 3/2006 | Guetta et al. | ............... | 356/237.2 |
| 2007/0058164 A1 * | 3/2007 | Shibata et al. | ............. | 356/237.2 |

OTHER PUBLICATIONS

Applied Materials Israel, Ltd.; Office Action from State Intellectual Property Office of The People's Republic of China in Chinese Patent Application No. 20070142879.3; Office Action mailed Jul. 26, 2010; 11pp.; (English Translation included).

Applied Materials Israel, Ltd.; Office Action from State Intellectual Property Office of The People's Republic of China in Chinese Patent Application No. 20070142879.3; Office Action mailed Aug. 31, 2011 9pp.; (English Translation included).

Applied Materials Israel, Ltd.; Office Action in Japanese Patent Application No. 2007-201013; Office Action mailed Dec. 1, 2011; 1pg.; (English Translation only).

* cited by examiner

*Primary Examiner* — Gregory J Toatley
*Assistant Examiner* — Rebecca C Bryant
(74) *Attorney, Agent, or Firm* — Tarek N. Fahmi

(57) ABSTRACT

A system, method and computer readable medium for reticle evaluation, the method includes: (i) obtaining, during an imaging process, multiple images of the reticle under different polarization and optionally interferometric conditions; and (ii) generating an output aerial image in response to (i) the multiple images and (ii) differences between the imaging process and an exposure process; wherein during the exposure process an image of the reticle is projected onto a wafer.

52 Claims, 5 Drawing Sheets

METHOD AND SYSTEM FOR AERIAL IMAGING OF A RETICLE

RELATED APPLICATIONS

This application claims the priority of U.S. Provisional Patent Application No. 60/821,056, filed date Aug. 1, 2006.

FIELD OF THE INVENTION

This invention is generally in the field of reticle inspection and especially reticle evaluation by aerial image emulating optics.

BACKGROUND OF THE INVENTION

Modern microelectronic devices are commonly produced using a photolithographic process. In this process, a semiconductor wafer is first coated with a layer of photoresist. This photoresist layer is then exposed (during a so-called exposure process) to illuminating light using a reticle (also called photo-mask, or a mask) and subsequently developed. Upon development, exposed positive photoresist is removed (alternatively, non-exposed negative photoresist is removed), and the remaining photoresist produces the image of the reticle on the wafer. Thereafter, the uppermost layer of the wafer is etched. Thereafter, the remaining photoresist is stripped. For multilayer wafers, the above procedure is then repeated to produce subsequent patterned layers.

It should be appreciated by those skilled in the art that to produce an operational semiconductor product, a reticle must be as defect-free as possible, preferably completely defect-free. Therefore, reticle evaluation tools are needed to detect various defects in the reticles that can potentially reduce the microelectronic circuit fabrication yields.

It is customary to relate the electric field just behind the mask (reticle) to the field of impinging light by a mask function. The notion of a mask function can be useful also for imaging and projection applying partially coherent light, where in that case the image formation is typically described by some variant of the Hopkins formula. For a mask with pattern features large compared with the illuminating wavelength, the Kirchoff boundary conditions, also known as the "thin mask approximation", can be safely used in order to compute the resulting aerial image or, alternatively, the intensity pattern on the wafer. However, once the features on the mask become comparable in size to the illuminating wavelength, as is the case with state-of-the-art current masks, this approximation is no longer valid, and the transmission of the mask becomes dependent on the polarization state and angle of incoming light.

For certain features which are common in modern reticles, typically ones possessing a high degree of spatial symmetry, the amplitude, phase and polarization state of diffracted light can be predicted, based, for example, on analytic results as well as efficient numerical models. For other reticle patterns, where such calculations are either very inefficient or too complicated, one may still use the knowledge of the reticle design, together with certain interferometric or wavefront-sensing technique, in order to obtain a sufficiently close approximation of the properties of the diffraction orders that carry most of the image power.

Rapid shrinking of feature size in semiconductor products has led to an increasing Numerical Aperture (NA) values in exposure systems such as steppers. Currently, the Numerical Apertures of exposure systems exceed one, are growing rapidly towards one point four and are expected to reach one point eight in the near future.

At high Numerical Aperture values which represent large angles of incidence, the exposure process is more susceptible to polarization related effects, especially those effects that occur at high angles of incidence of the light upon the resist.

Aerial imaging tools, such as aerial inspection tools and aerial review tools, try to mimic the exposure process while applying an imaging process that differs from the exposure process. While during the exposure process the image of the reticle is de-magnified, during the imaging process the image of the reticle is magnified. This magnification results in a decrement of the angles of incidence by the same magnification factor, which can be around several hundreds. The consequence of this magnification process is that polarization effects that occur on the wafer plane are not emulated by the aerial imaging system. Especially, an exposure process substantially reduces the contrast ratio of p-polarized light (also referred to as TM) in relation to the contrast ratio of s-polarized light (also referred to as TE), while an imaging process does not perform such a reduction.

FIGS. 1 and 2 illustrate the difference between p-polarized light components and s-polarized light components.

FIG. 1 illustrates an exposure system 10 that includes light source 12 that provides s-polarized light. The diffraction creates two or more coherent rays (such as rays 15a and 15b of FIG. 1), that appear at different locations on the pupil plane, each arriving at the image plane from a different direction.

As the coherent rays hit the wafer from different directions, all their fields vectors combine in a vector superposition manner, to create the point electric field.

The aerial image is the intensity of this field. The angular difference between the two incident beams creates the high-angle polarization effect.

Light source 12 is followed by reticle 14 and by objective lens 16. S-polarized light passes through transparent portions of reticle 14 towards objective lens 16 that projects an image of reticle 14 onto wafer 20. The electric field vector of the s-polarized light is perpendicular to the plane of FIG. 1. Extract 30 is a top view of the electric field vector of radiation of the s-polarized light at the pupil plane, or at an upper portion of objective lens 16, while extract 32 is a side view of the coherent light rays 42 and 44 at the wafer (or image) plane. Two dots 46 and 48 represent the direction of the field vectors of these light rays.

FIG. 2 illustrates the same configuration as an exposure system 10 but light source 12 provides p-polarized light. The intensity vector of the p-polarized light appears in the plane of FIG. 1. Extract 34 is a top view of the electric field vector of radiation of the p-polarized light at an upper portion of objective lens 16 while extract 36 is a side view of the coherent light rays 52 and 54 at the wafer plane. Two dots 56 and 58 represent the field vector associated with these light rays. It is noted that every illumination source may be described as generating radiation rays that include both S and P polarizations components.

The aerial image is the square self dot product of the electric field vector of light that impinges on a wafer or on a sensor. The electric field can be divided into two independent polarization components—p-polarized (TM) component and s-polarized (TE) component. The theory of imaging at high values of numerical aperture indicates that the vector sum of s-polarized light is markedly different from that of p-polarized light, due to the large angles of incidence encountered at high Numerical Aperture projection. Indeed, while the angle between the electric field vectors of two s-polarized beams that converge on the image plane from different directions is independent of the polar angles of the beams (the angles between the beams and the system's optical axis), this is certainly not the case for two p-polarized such beams. This implies a strong dependence of the contrast of images formed by p-polarized light on the angle of incidence at the image plane. As the typical feature size on the photo-mask shrinks, light converging at high angles of incidence carries the significant fraction of the power at the spatial frequencies required for successful image formation, whence the critical dependence on the beams at the extreme angles of incidence.

Moreover, at NA values exceeding ~0.7, both regimes give rise to images whose properties may deviate significantly from those obtained with low numerical aperture imaging, owing to the enhancement of the relative power carried by converging beams of high angle of incidence.

While projection systems of an exposure process typically employ very high angles of incidence, the large magnification applied by the imaging process results in light that converges on the image plane with much smaller angles of incidence. This fundamental difference results in different images produced by the same mask pattern on the wafer and at the image plane of the exposure system and imaging system, respectively.

These differences between the exposure process and the imaging process should be compensated for in order to enable imaging systems to mimic the exposure process in a reliable manner.

There is a need to provide efficient systems and methods for reticle evaluation.

SUMMARY OF THE INVENTION

A method for reticle evaluation, the method including: (i) obtaining, during an imaging process, multiple images of the reticle under different polarization conditions; and (ii) generating an output aerial image in response to (i) the multiple images and (ii) differences between the imaging process and an exposure process, wherein during the exposure process an image of the reticle is projected onto a wafer.

A computer readable medium having computer-readable code embodied therein for reticle evaluation, the computer-readable code including instructions for: obtaining, during an imaging process, multiple images of the reticle under different polarization conditions; and generating an output aerial image in response to (i) the multiple images and (ii) differences between the imaging process and an exposure process, wherein during the exposure process an image of the reticle is projected onto a wafer.

A system for reticle evaluation, the system including: a memory unit adapted to store information representative of multiple images of a reticle, and a processor, connected to the memory unit, the processor is adapted to: receive the information representative of the multiple images, wherein the multiple images are acquired during an imaging process and under different polarization conditions; and generate an output aerial image in response to (ii) the multiple images and (ii) differences between the imaging process and an exposure process, wherein during the exposure process an image of the reticle is projected onto a wafer.

A method for aerial imaging, the method including: controlling, during an imaging process, an intensity and polarization of multiple light rays to define reticle illumination conditions that are substantially equal to illumination conditions of the reticle during an exposure process, wherein during the exposure process an image of the reticle is projected onto a wafer; and acquiring an image of the reticle.

A system, including: imaging optics, adapted to apply an imaging process while controlling, during the imaging process, an intensity and polarization of multiple light rays to define reticle illumination conditions that are substantially equal to illumination conditions of the reticle during an exposure process, wherein during the exposure process an image of the reticle is projected onto a wafer; and a sensor, adapted to acquire an image of the reticle.

BRIEF DESCRIPTION OF THE DRAWINGS

In order to understand the invention and to see how it may be carried out in practice, an embodiment will now be described, by way of non-limiting example only, with reference to the accompanying drawings, in which.

DETAILED DESCRIPTION OF EXEMPLARY EMBODIMENTS

Figure 1:
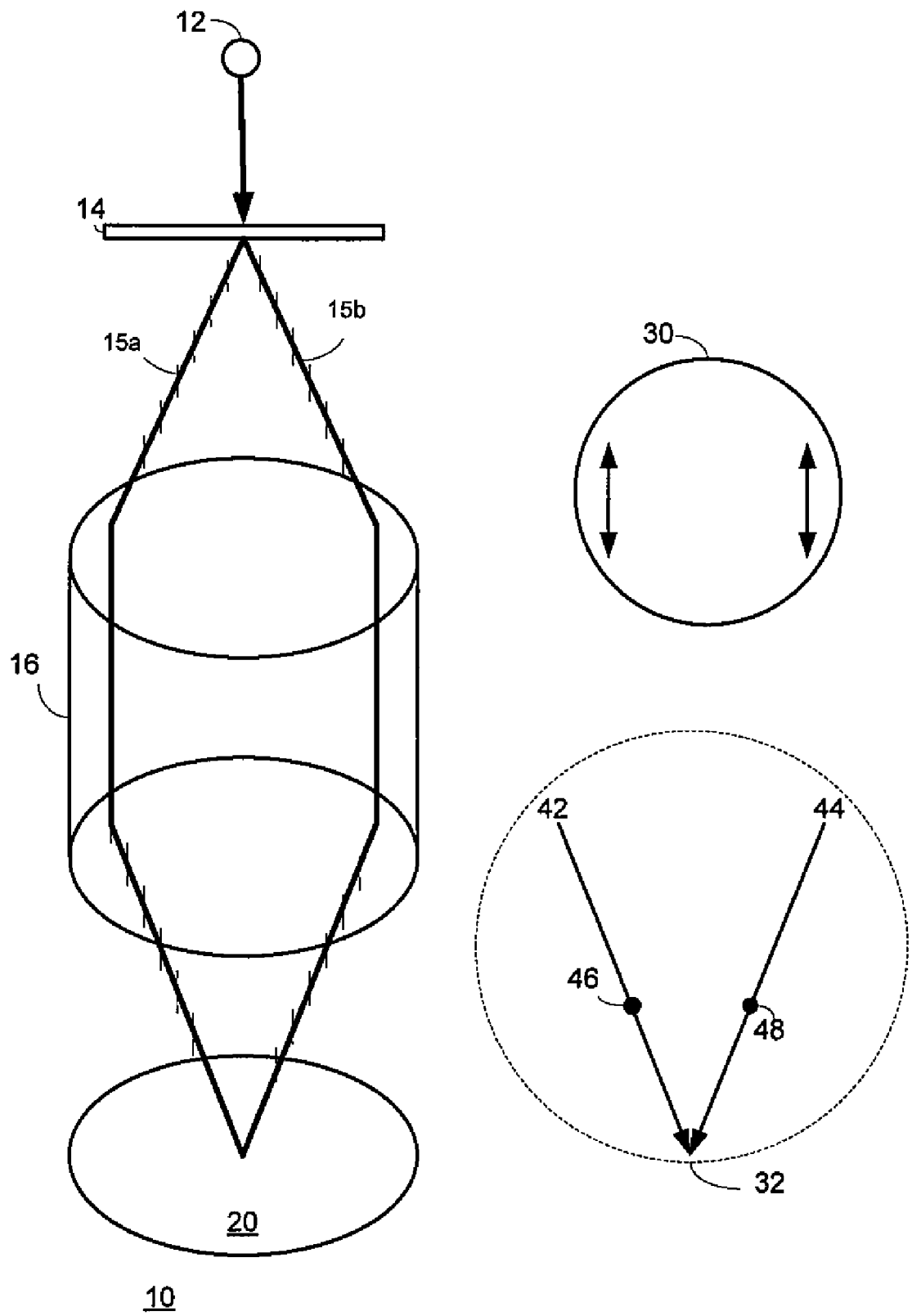
FIGS. 1 and 2 illustrate the difference between p-polarized light components and s-polarized light components that pass through an exposure system.
Figure 2:
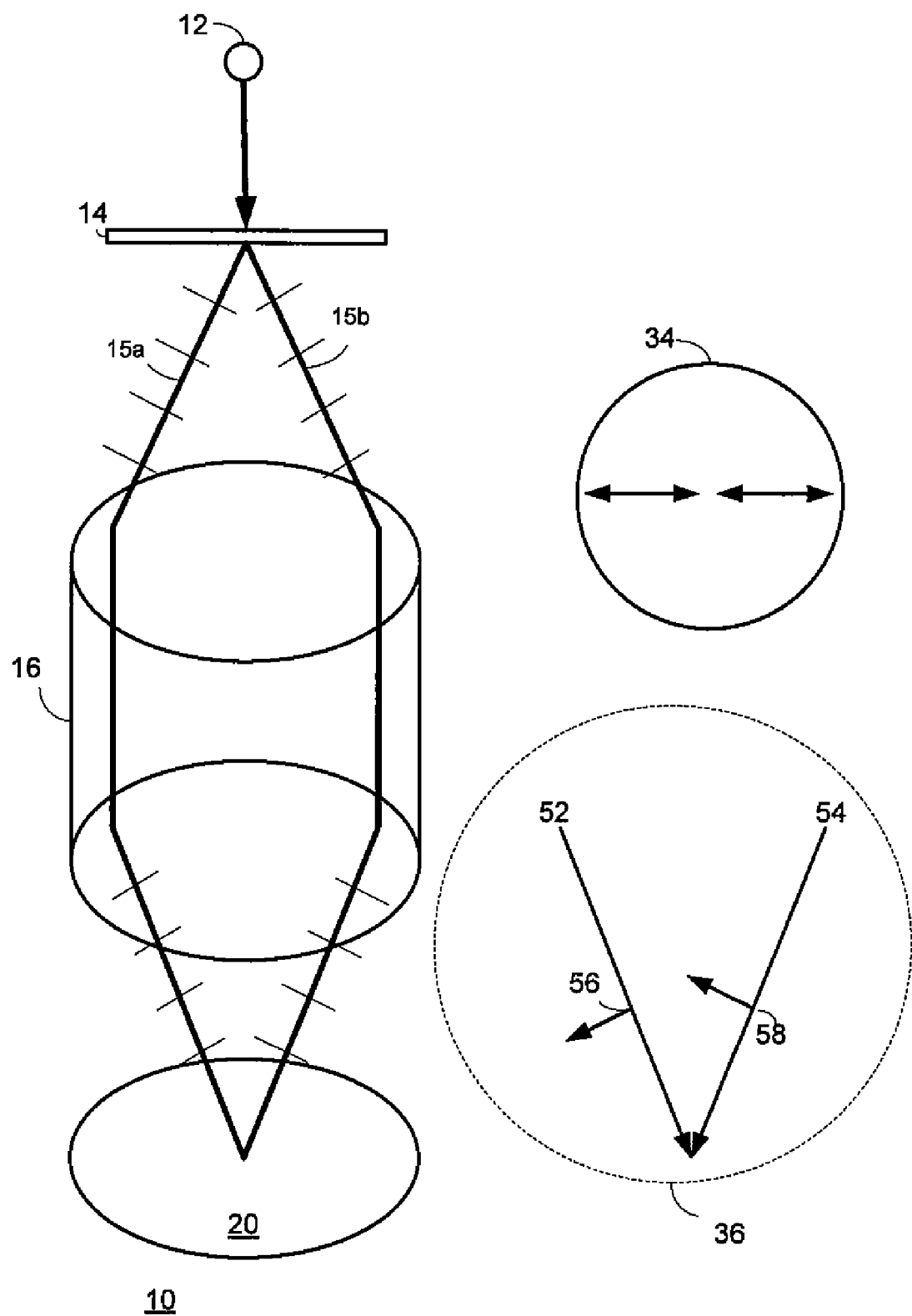

The term "reticle" can be interpreted according to its conventional meaning as well as meaning a reticle or a mask. A reticle generally includes a transparent substrate and a layer of opaque material (such as chrome) is formed thereon. A reticle may also include a reticle, one or more additional materials formed under the opaque material such as an adhesion layer, anti-reflective layer, phase shift layer, attenuation layer and the like. Typical reticles include binary reticles, reticles that include optical proximity correction features, phase-shift masks (PSM), ternary attenuated PSM, alternating PSM, attenuated PSM, halftone PSM, clear-field reticle, and dark-field reticle.

As used herein, the term "exposure system" generally refers to any lithography system that prints images of a reticle onto a specimen using electromagnetic radiation. The exposure system may include a stepper, a scanning projection system or a step-and-repeat system. An exposure process is the lithographic process applied by the exposure system.

As used herein, the term "imaging system" generally refers to a system that generates an image of a reticle. An imaging system may be a reticle evaluation system such as a reticle inspection system, a reticle review system or a reticle metrology system. The imaging system applies an imaging process.

It is noted that all figures are out of scale.

A system, method and computer program product for reticle evaluation is provided.

The system, method and computer program product compensate for differences between the exposure process and the imaging process by receiving or acquiring at least one image, wherein if multiple images are acquired then each is acquired under different polarization conditions and optionally also under different phase (interferometric) conditions. The differences between the polarization (and optionally phase) conditions enable one to isolate TM and TE components of the aerial image, then to apply a corrective transformation on the TM and TE images, and add the corrected TE and TM components with an appropriate weight to create an output aerial image.

It is noted that one aerial image can be obtained while filtering out the TM component while the other can be obtained while filtering out the TE component, but this is not necessarily so. For example, at least one aerial image can include both components. Assuming that the different polarization (and optionally phase) conditions are known, the TE and TM components can be extracted.

The images can be obtained by using one or more polarizing components in the illumination channel and/or in the collection channel.

Conveniently, the collection channel includes a polarization (and optionally phase) filter (or filters) at the aperture plane. The exact details of these polarization (and optionally phase) filter (or filters) depend on the certain illumination conditions and pattern on the mask.

It is noted that for simplicity of explanation the following explanation mainly refers to polarization. It is noted that according to various embodiments of the invention the systems and methods are also responsive to phase differences. Thus, phase retarders, phase shifters and phase affecting elements can be used, as well as using phase responsive aerial imaging processing that can compensate for phase related differences between an imaging process and an exposure process.

Conveniently, both the collection channel and the illumination channel include a polarization filter.

Once the TM and TE components of the aerial image are determined, they undergo a compensation process. The compensation process includes decomposing the TE and TM components of the aerial image into their spatial spectral components. The decomposition can involve applying a Fourier transform. One or more spectral components are corrected using a correction function, and then a weighted inverse function is applied in order to provide the corrected polarization components of the aerial image. The corrected TE and TM components are then summed to provide a so-called output aerial image.

Figure 3:
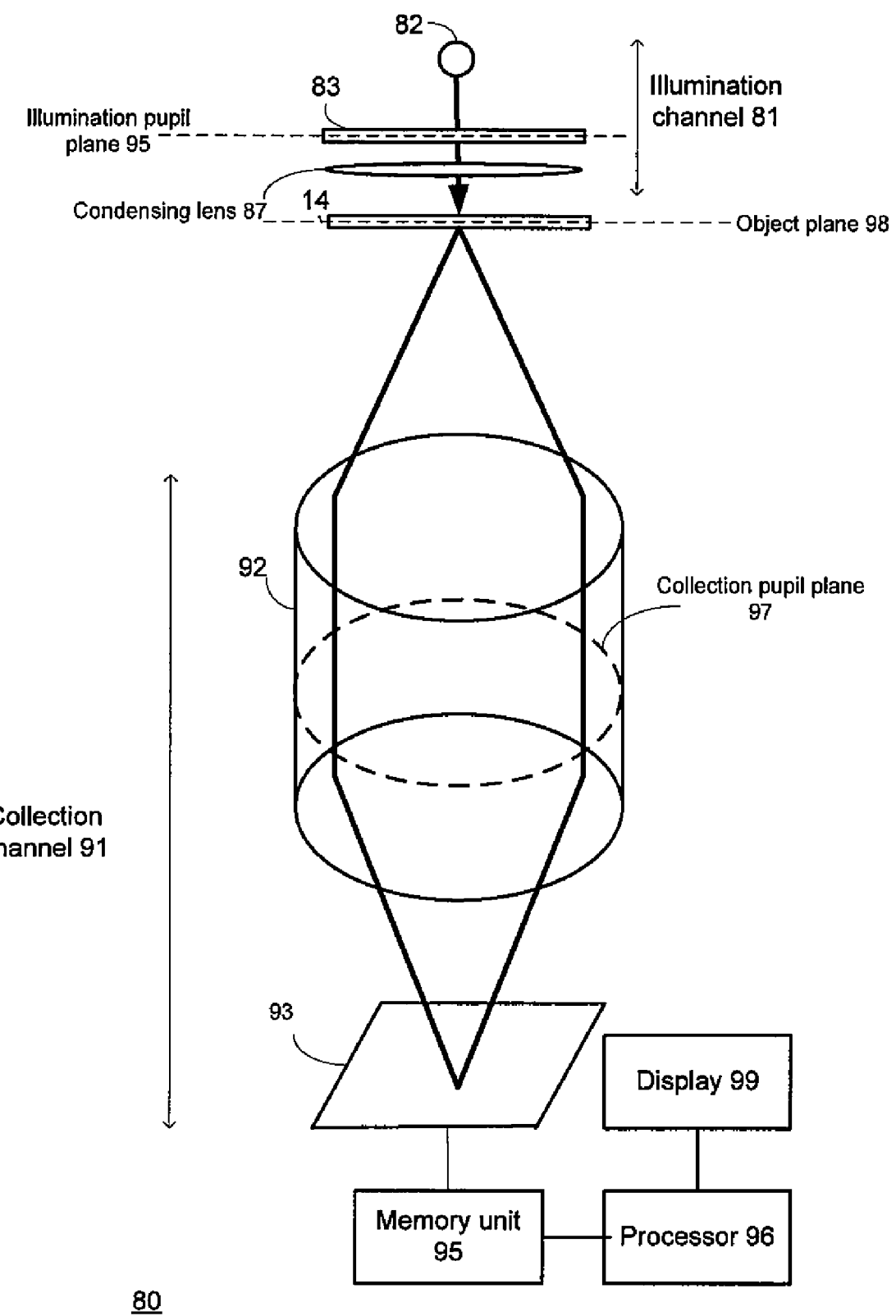
FIG. 3 illustrates a system according to an embodiment of the invention.

FIG. 3 illustrates imaging system 80, according to an embodiment of the invention.

According to an embodiment of the invention imaging system 80 is provided. Imaging system 80 includes illumination channel 81 and collection channel 91. Illumination channel 81 includes light source 82 and condensing lens 87. Collection channel 91 includes objective lens 92 and camera 93.

According to an embodiment of the invention illumination channel 81 also includes a polarizer 83. It is noted that a phase retrieval method may also require separating the illumination channel into several sub-channels (corresponding to several beams).

For simplicity of explanation FIG. 3 illustrates a single polarizer 83 that belongs to the illumination path as well as a single camera 93.

Conveniently, mask 14 is located at an object plane 98 and polarizer 83 is located at an illumination pupil plane 95. Reticle 14 and polarizer 83 are located a focal length away from condensing lens 87.

It is noted that, additionally or alternatively, collection channel 91 can include one or more polarizers. It is noted that knowledge of relative phase between coherent beams that are incident on the image plane from different directions may require some sort of interferometry, whence the system can include phase filters, phase plates and the like.

According to an embodiment of the invention by polarizer 83 can control the intensity and polarization of light at the illumination pupil plane 95. Thus, it actually controls the polarization and intensity of light rays of different incidence angles. Especially, the polarization and the attenuation can be determined across the pupil.

Conveniently, the polarization and intensity of multiple points over the illumination pupil plane can be controlled.

It is further noted that the collection channel 91 can include a Bertrand lens before the camera, such that the image acquired is the image of pupil plane 97 (also known as a Bertrand image).

It is further noted that collection channel 91 can include multiple cameras that can acquire multiple aerial images simultaneously.

According to an embodiment of the invention the cameras acquire images that differ by their focal conditions. For example, one camera can acquire a focused image while another camera can acquire an out of focus image.

According to another embodiment of the invention the cameras acquire images that differ by their polarization conditions. While one camera acquires an image that is projected on a certain polarization another camera can acquire an image that is projected on another polarization.

Those of skill in the art will appreciate that a combination of different focus and polarization conditions can also be imposed by the imaging system.

Camera 93 sends information representative of acquired images to memory unit 95. Memory unit 95 is connected to processor 96. Processor 96 is connected to memory unit 95 and is adapted to: (i) receive the information representative of the multiple images, wherein the multiple images are acquired under different polarization conditions; and (ii) generate an output aerial image in response to the multiple images which will compensate for the differences between an aerial image (or image set) and the result of the exposure process during which an image of the reticle is projected onto a wafer.

Figure 4:
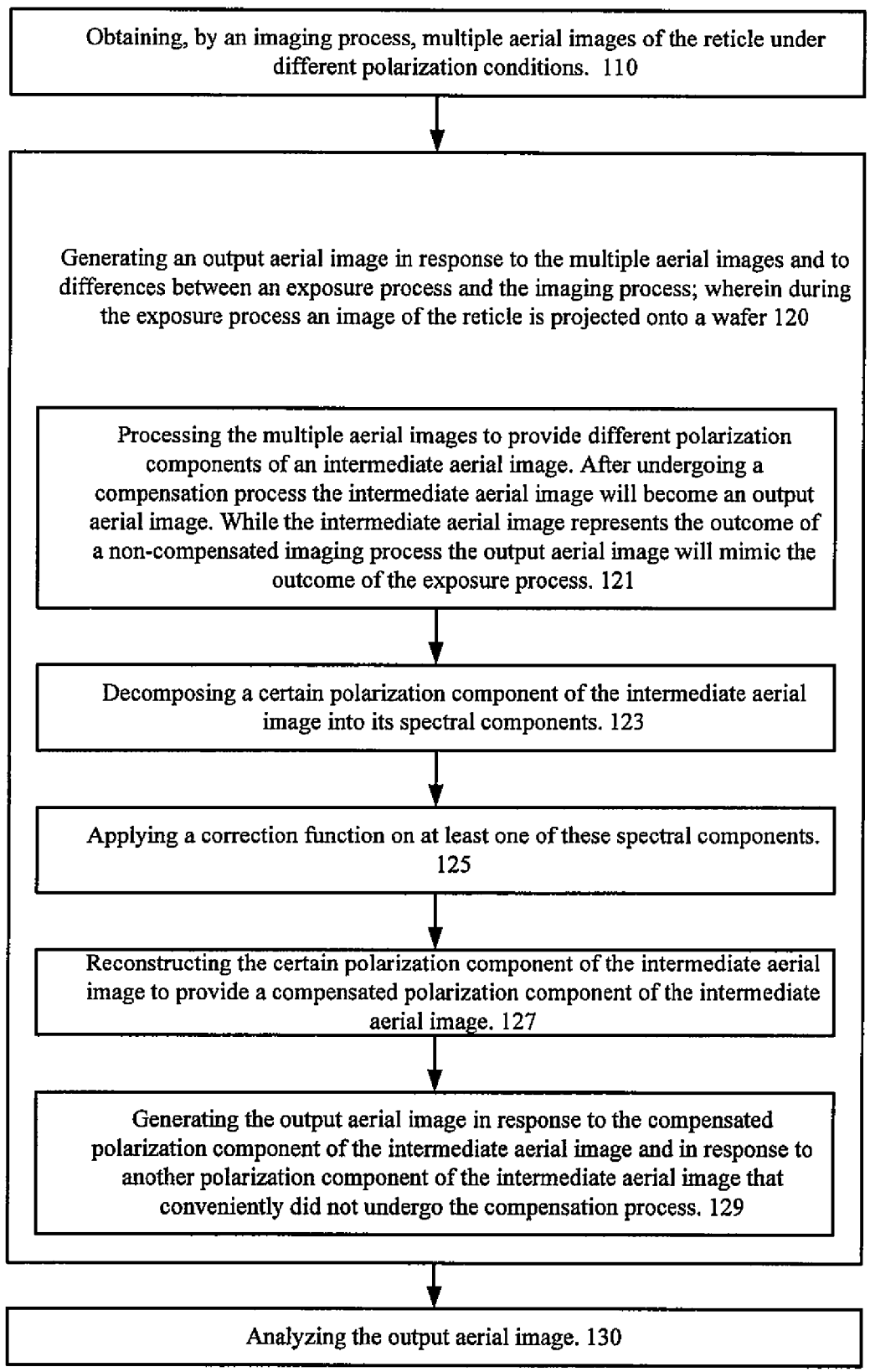
FIG. 4 illustrates a method according to an embodiment of the invention.

Processor 96 can also analyze the aerial image, as further illustrated in FIG. 4. The analysis can include performing die to die comparison, die to database comparison, determining process windows, evaluating critical dimensions of reticle features, evaluating critical dimensions of features printed by an exposure process, determine a printability of reticle defects, generate a defect map, generate a signature map, perform statistical analysis of defects or features, and the like.

Imaging system 80 also includes a display 99 that can display the output aerial image as well as information representative of an analysis of the output aerial image. For example, display 99 can be used for displaying a map of possible defects that can be displayed.

According to another embodiment of the invention the processing of the images is executed by a remote processor that receives information representative of the multiple images (acquired under different polarization conditions) and performs the above mentioned operations.

FIG. 4 illustrates method 100 for reticle evaluation, according to an embodiment of the invention.

Method 100 starts by stage 110 of obtaining during an imaging process multiple images of the reticle under different polarization (and optionally phase) conditions. This can be achieved by using one or more polarizing components, and optionally one or more phase elements and retarders, and the like. It is further noted that an obtained image may as well be a Bertrand image. It is further noted that an obtained image may as well be an image acquired at a different location.

Stage 110 can include at least one of the following or a combination thereof: (i) utilizing multiple detection channels, each characterized by different polarization (and optionally phase) characteristics, (ii) obtaining the multiple images while altering polarization characteristics (and optionally optical path difference) of an illumination channel, (iii) altering polarization characteristics and optionally optical path of a detection channel and of an illumination channel.

Stage 110 is followed by stage 120 of generating an output aerial image in response to the multiple images, and in response to differences between the imaging process and an exposure process. During the exposure process an image of the reticle is projected onto a wafer.

Conveniently, stage 120 may include compensating for these differences.

It is noted that the transformation between the exposure process to the imaging process can be computed and stored to be later used for processing one or more other images.

According to an embodiment of the invention stage 120 includes generating the output aerial image responsive to polarization and optionally phase dependent characteristics of the exposure process and of the imaging process. Conveniently, the exposure process and the imaging process react in a different manner to p-polarized light and to s-polarized light. In particular, the exposure process results in intensity patterns on the wafer, which, in general, have contrast different from images produced by the imaging system, and which, furthermore, is highly dependent on the polarization state of the light. The generation of the output aerial image should take into account this difference.

Conveniently, stage 120 includes sub-stages 121-129.

Stage 121 includes processing the multiple images to provide different polarization components of an intermediate image. After undergoing a compensation process the intermediate image will become an output aerial image. While the intermediate image represents the outcome of a non-compensated imaging process the output aerial image will mimic the outcome of the exposure process.

Stage 121 is followed by stage 123 of decomposing a certain polarization component of the intermediate image into its spatial spectral components.

Stage 123 can involve applying a Fourier transform, although other decomposition functions can be applied.

Stage 123 is followed by stage 125 of applying a correction function on at least one of these spectral components.

Stage 125 includes applying a correction function in response to at least one polarization dependent characteristic. It can also include at least one of the following or a combination thereof: (i) applying the correction function on a single spectral component, (ii) applying the correction function on a single spectral component that corresponds to a pitch of a repetitive pattern of the reticle, (iii) applying on a spectral component a correction function that is inversely proportional to a square of a spectral frequency of the spectral component, (iv) applying a correction function that is responsive to angle between incident rays.

Figure 5:
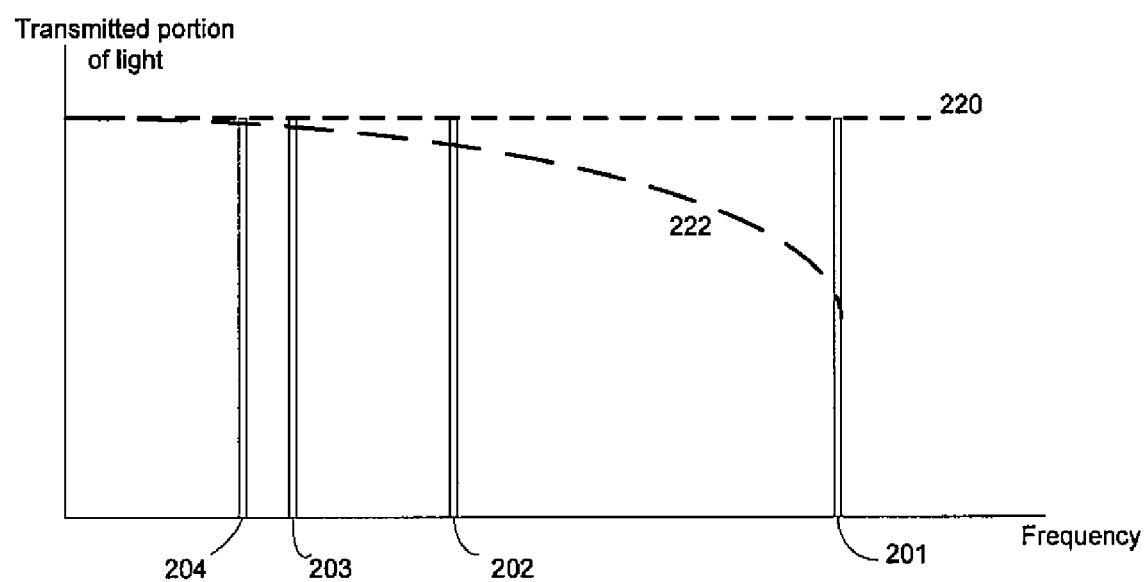
FIG. 5 illustrates a relationship between spectral components of an s-polarized component of an intermediate image and an attenuation of these spectral components according to an embodiment of the invention.

FIG. 5 illustrates a relationship between spectral components 201-204 of an s-polarized component of an intermediate image and an attenuation of these spectral components according to an embodiment of the invention.

The frequency of spectral component 201 corresponds to a pitch of a repetitive pattern of the reticle. The other spectral components correspond to multiplications of this pitch.

Horizontal curve 220 illustrates the response of an imaging system to the s-polarized light while curve 222 illustrates the response of an exposure system to the s-polarized light. The difference between these curves illustrates the attenuation of these spectral components. The attenuation is typically inversely proportional to a square of these frequencies. Because the first spectral component 201 is relatively spaced away from other spectral components it is dramatically attenuated in relation to the other spectral components.

In order to simplify the compensation process and enable real time or almost real time compensation the compensation process can focus on the first spectral component.

Conveniently, each spectral component of the decomposed image represents the result of interference of two (or more) different coherent fields, approaching from different directions which are separated by a certain angle of incidence. The result of the interference is proportional to the square of the vector sum of the interfering electric fields. This relation can be derived from the design scheme of the imaging system. Under certain conditions, which exist in new generation exposure systems, it can be shown that each spectral component passes a linear process of contrast modification, which depends on the angle between incident rays and on their polarization state. This is accompanied by a modification of fractional spectral power carried by the different spectral components—a process to which the high frequency spectral components are particularly prone. A simple wafer resist model, together with optical modeling, can be used to derive and calibrate this linear relationship. After applying this linear correction transformation in Fourier-space, a weighted vector sum of all frequency components is inverted, in order to receive the expected image of the TE and TM polarization components.

Referring back to FIG. 4, stage 125 is followed by stage 127 of reconstructing the certain polarization components of the intermediate image to provide a compensated polarization components of the intermediate image.

Stage 127 is followed by stage 129 of generating the output aerial image in response to the compensated polarization components of the intermediate image and in response to another polarization component of the intermediate image that conveniently did not undergo the compensation process. It is noted that in many cases both polarization components of the intermediate image can undergo a compensation process. Conveniently, stage 129 includes summing the polarization components of the intermediate image.

Stage 120 can be followed by stage 130 of analyzing the output aerial image. The analysis can involve at least one of the following or a combination thereof: (i) estimating critical dimensions of feature of wafers manufactured by the exposure process, (ii) estimating critical dimensions of reticle features, (iii) evaluating a process window of the exposure process, and (iv) determining out of focus polarization characteristics of the imaging process in response to focus measurements.

Each of the various aforementioned methods can be executed by a computer that executes a computer program stored in a computer readable medium. Accordingly, a computer readable medium is provided. The computer readable medium has computer-readable code embodied therein for reticle evaluation, the computer-readable code including instructions for: obtaining multiple images of the reticle under different polarization conditions; and generating an output aerial image in response to the multiple images and to differences between an exposure process during which an image of the reticle is projected onto a wafer and an imaging process during which the multiple images were obtained.

Conveniently, the computer-readable code includes instructions for: decomposing a certain polarization component of an image into its spectral components, and applying a correction function on at least one spectral component; wherein the correction function is responsive to at least one polarization dependent characteristic.

Conveniently, the computer-readable code includes instructions for applying the correction function on a single spectral component.

Conveniently, the reticle includes a repetitive pattern and wherein the computer-readable code includes instructions for applying the correction function on a single spectral component that corresponds to a pitch of the repetitive pattern.

Conveniently, the computer-readable code includes instructions for applying the correction function on a single spectral component that corresponds to a pitch of the repetitive pattern.

Conveniently, the computer-readable code includes instructions for applying on a spectral component a correction function that is inversely proportional to a square of a spectral frequency of the spectral component.

Conveniently, the correction function is responsive to an angle between incident rays.

Conveniently, the computer-readable code includes instructions for utilizing multiple detection channels, each characterized by different polarization characteristics determined by controlling a polarization and an intensity of light at a collection pupil plane.

Conveniently, the computer-readable code includes instructions for obtaining the multiple images while altering polarization characteristics of an illumination channel by controlling a polarization and an intensity of light at an illumination pupil plane.

Conveniently, the computer-readable code includes instructions for altering polarization characteristics of a detection channel and of an illumination channel by controlling a polarization and an intensity of light at a pupil plane.

Conveniently, the computer-readable code includes instructions estimating critical dimensions of features of wafers manufactured by the exposure process.

Conveniently, the computer-readable code includes instructions for estimating critical dimensions of reticle features.

Conveniently, the computer-readable code includes instructions for evaluating a process window of the exposure process.

Conveniently, the computer-readable code includes instructions for determining out of focus polarization characteristics of the imaging process in response to focus measurements.

Conveniently, the computer-readable code includes instructions for generating a defect map of the reticle.

Conveniently, the computer-readable code includes instructions for generating the output aerial image in response to phase retardation characteristics of the exposure process and of the imaging process.

Those skilled in the art will readily appreciate that various modifications and changes can be applied to the embodiments of the invention as herein before described without departing from its scope defined in and by the appended claims.

We claim:

1. A method, comprising:
    obtaining, during an imaging process, multiple aerial images of a reticle under different polarization conditions, the aerial images generated by light transmitted through the reticle; and
    generating an output aerial image by processing the multiple aerial images to compensate for differences between the imaging process and an exposure process, the exposure process referring to an image of the reticle being projected onto a wafer, wherein the processing of the multiple aerial images comprises:
        decomposing a certain polarization component of at least one of the multiple aerial images into its spectral components,
        attenuating at least one of the spectral components, wherein the attenuating compensates for at least some of the differences between the imaging process and the exposure process,
        reconstructing the certain polarization component based on the at least one attenuated spectral component, and
        generating the output aerial image based on the reconstructed polarization component.

2. The method according to claim 1, wherein the differences comprise differences between polarization dependent characteristics of the exposure process and of the imaging process.

3. The method according to claim 2, wherein the polarization dependent characteristics of the exposure process represent a polarization dependent transfer function of the exposure process.

4. The method according to claim 1, wherein the generating of the output aerial image comprises attenuating a single one of the spectral components.

5. The method according to claim 1, wherein the reticle comprises a repetitive pattern and wherein the generating of the output aerial image comprises attenuating a single spectral component that corresponds to a pitch of the repetitive pattern, wherein a frequency of the single spectral component corresponds to the pitch.

6. The method according to claim 5, wherein the attenuation is inversely proportional to a square of a spectral frequency of the single spectral component.

7. The method according to claim 1, wherein the compensation is responsive to an angle between a plurality of rays incident on a surface of a sensor, wherein the plurality of rays include the light transmitted through the reticle.

8. The method according to claim 1, wherein the obtaining comprises utilizing multiple detection channels, each characterized by different polarization characteristics determined by controlling a polarization and intensity of light at a collection pupil plane.

9. The method according to claim 1, wherein the obtaining comprises obtaining the multiple aerial images while altering polarization characteristics of an illumination channel by controlling a polarization and intensity of light at an illumination pupil plane.

10. The method according to claim 1, wherein the obtaining comprises obtaining the multiple aerial images while altering polarization characteristics of an illumination that is selected from a coherent illumination, a non-coherent illumination, a partially coherent illumination or a combination of multiple coherent modes.

11. The method according to claim 1, wherein the obtaining comprises altering polarization characteristics of a detection channel and of an illumination channel by controlling a polarization and an intensity of light at a pupil plane.

12. The method according to claim 1, further comprising estimating critical dimensions of features of wafers manufactured by the exposure process.

13. The method according to claim 1, further comprising estimating critical dimensions of features of the reticle.

14. The method according to claim 1, further comprising evaluating a process window of the exposure process.

15. The method according to claim 1, further comprising determining out of focus polarization characteristics of the imaging process.

16. The method according to claim 1, further comprising generating a defect map of the reticle.

17. The method according to claim 1, wherein the output aerial image is generated in further response to phase retardation characteristics of the exposure process and of the imaging process.

18. The method according to claim 1, wherein the obtaining comprises utilizing multiple detection channels, each characterized by different polarization and phase retardation characteristics determined by controlling a polarization, an optical path and an intensity of light at a collection pupil plane.

19. A system, comprising:
a memory unit adapted to store information representative of multiple aerial images of a reticle;
a processor coupled to the memory unit; and
computer-readable code stored in the memory unit, wherein the computer-readable code, when executed by the processor, causes the processor to:
receive the information representative of the multiple aerial images, wherein the multiple aerial images are acquired during an imaging process and under different polarization conditions; and
generate an output aerial image by processing the multiple aerial images to compensate for differences between the imaging process and an exposure process,
the exposure process referring to an image of the reticle being projected onto a wafer, wherein the processing of the multiple aerial images comprises:
decomposing a certain polarization component of one of the multiple aerial images into its spectral components,
attenuating at least one of the spectral components, wherein the attenuating compensates for at least some of the differences between the imaging process and the exposure process,
reconstructing the certain polarization component based on the at least one attenuated spectral component, and
generating the output aerial image based on the reconstructed polarization component.

20. The system according to claim 19, wherein the differences comprise differences between polarization dependent characteristics of the exposure process and of the imaging process.

21. The system according to claim 20, wherein the polarization dependent characteristics of the exposure process represent a polarization dependent contrast ratio of intensity patterns on the wafer, which would be present during the exposure process.

22. The system according to claim 19, wherein the computer-readable code further causes the processor attenuate a single one of the spectral components.

23. The system according to claim 19, wherein the reticle comprises a repetitive pattern, wherein the computer-readable code further causes the processor to attenuate a single spectral component that corresponds to a pitch of the repetitive pattern, and wherein a frequency of the single spectral component corresponds to the pitch.

24. The system according to claim 23, wherein the attenuation is inversely proportional to a square of a spectral frequency of the single spectral component.

25. The system according to claim 19, wherein the compensation is responsive to an angle between a plurality of rays incident on a surface of a sensor, wherein the plurality of rays include the light transmitted through the reticle.

26. The system according to claim 19, wherein the computer-readable code further causes the processor to generate the output aerial image in response to p-polarized components of at least one of the multiple aerial images.

27. The system according to claim 19, further comprising multiple detection channels, each characterized by different polarization characteristics that are determined by controlling a polarization and an intensity of light at a collection pupil plane.

28. The system according to claim 19, adapted to obtain the multiple aerial images while altering polarization characteristics of an illumination channel by controlling a polarization and an intensity of light at an illumination pupil plane.

29. The system according to claim 19, adapted to alter polarization characteristics of a detection channel and of an illumination channel by controlling a polarization and an intensity of light at a pupil plane.

30. The system according to claim 19, wherein the computer-readable code further causes the processor to estimate critical dimensions of features of wafers manufactured by the exposure process.

31. The system according to claim 19, wherein the computer-readable code further causes the processor to estimate critical dimensions of features of the reticle.

32. The system according to claim 19, wherein the computer-readable code further causes the processor to evaluate a process window of the exposure process.

33. The system according to claim 19, wherein the computer-readable code further causes the processor to determine out of focus polarization characteristics of the imaging process.

34. The system according to claim 19, wherein the computer-readable code further causes the processor to generate the output aerial image in further response to phase retardation characteristics of the exposure process and of the imaging process.

35. The system according to claim 19, further comprising multiple detection channels, each characterized by different polarization and phase retardation characteristics determined by controlling a polarization, an optical path and an intensity of light at a collection pupil plane.

36. A computer readable medium having computer-readable code comprising instructions for:
obtaining, during an imaging process, multiple aerial images of a reticle under different polarization conditions; and
generating an output aerial image of the reticle by processing the multiple aerial images to compensate for differences between the imaging process and an exposure process, the exposure process referring to an image of the reticle being projected onto a wafer, wherein the processing of the multiple aerial images comprises:
decomposing a certain polarization component of at least one of the multiple images into its spectral components,
attenuating at least one of the spectral components, wherein the attenuating compensates for at least some of the differences between the imaging process and the exposure process,
reconstructing the certain polarization component based on the at least one attenuated spectral component, and
generating the output aerial image based on the reconstructed polarization component.

37. The computer readable medium of claim 36, wherein the computer-readable code further comprises instructions for attenuating a single one of the spectral components.

38. The computer readable medium of claim 36, wherein the reticle comprises a repetitive pattern.

39. The computer readable medium of claim 38, wherein the generating of the output aerial image comprises attenuating a single spectral component that corresponds to a pitch of the repetitive pattern, wherein a frequency of the single spectral component corresponds to the pitch.

40. The computer readable medium of claim 38, wherein the attenuation is inversely proportional to a square of a spectral frequency of one of the spectral components.

41. The computer readable medium of claim 38, wherein the compensation is responsive to an angle between a plurality of incident rays incident upon a surface of a sensor, wherein the plurality of rays include the light transmitted through the reticle.

42. The computer readable medium of claim 36, wherein the computer-readable code further comprises instructions for utilizing multiple detection channels, each characterized by different polarization characteristics determined by controlling a polarization and an intensity of light at a collection pupil plane.

43. The computer readable medium of claim 36, wherein the computer-readable code further comprises instructions for obtaining the multiple aerial images while altering polarization characteristics of an illumination channel by controlling a polarization and an intensity of light at an illumination pupil plane.

44. The computer readable medium of claim 36, wherein the computer-readable code further comprises instructions for altering polarization characteristics of a detection channel and of an illumination channel by controlling a polarization and an intensity of light at a pupil plane.

45. The computer readable medium of claim 36, wherein the computer-readable code further comprises instructions for estimating critical dimensions of features of wafers manufactured by the exposure process.

46. The computer readable medium of claim 36, wherein the computer-readable code further comprises instructions for estimating critical dimensions of features of the reticle.

47. The computer readable medium of claim 36, wherein the computer-readable code further comprises instructions for evaluating a process window of the exposure process.

48. The computer readable medium of claim 36, wherein the computer-readable code further comprises instructions for determining out of focus polarization characteristics of the imaging process.

49. The computer readable medium of claim 48, wherein the computer-readable code further comprises instructions for generating a defect map of the reticle.

50. The computer readable medium of claim 36, wherein the computer-readable code further comprises instructions for generating the output aerial image in further response to phase retardation characteristics of the exposure process and of the imaging process.

51. A method, comprising:
controlling, during an imaging process to obtain an aerial image of a reticle, an intensity and a polarization of multiple light rays to define reticle illumination conditions that mimic illumination conditions of the reticle during an exposure process, the exposure process referring to an image of the reticle being projected onto a wafer;
acquiring the aerial image of the reticle from the multiple light rays; and
processing the acquired aerial image to compensate for differences between the imaging process and the exposure process, wherein the processing comprises:
decomposing a certain polarization component of the aerial image into its spectral components,
attenuating at least one of the spectral components, wherein the attenuating compensates for at least some of the differences between the imaging process and the exposure process,
reconstructing the certain polarization component based on the at least one attenuated spectral component, and
generating an output aerial image based on the reconstructed polarization component.

52. A system, comprising:
imaging optics adapted to apply an imaging process to obtain an aerial image of a reticle while controlling, during the imaging process, an intensity and a polarization of multiple light rays to define reticle illumination conditions that mimic illumination conditions of the reticle during an exposure process, the exposure process referring to an image of the reticle being projected onto a wafer;
a sensor adapted to acquire the aerial image of the reticle from the multiple light rays;
a memory unit;
a processor coupled to the memory unit; and
computer-readable code stored in the memory unit, wherein the computer-readable code, when executed by the processor, causes the processor to process the acquired aerial image to compensate for differences between the imaging process and the exposure process, wherein the processing comprises:
decomposing a certain polarization component of the aerial image into its spectral components,
attenuating at least one of the spectral components, wherein the attenuating compensates for at least some of the differences between the imaging process and the exposure process,
reconstructing the certain polarization component based on the at least one attenuated spectral component, and
generating an output aerial image based on the reconstructed polarization component.

* * * * *